United States Patent
Ohara et al.

(10) Patent No.: US 9,669,063 B2
(45) Date of Patent: Jun. 6, 2017

(54) COMPOSITION FOR PREVENTION, AMELIORATION OR TREATMENT OF METABOLIC SYNDROME

(71) Applicant: MORISHITA JINTAN CO., LTD., Osaka (JP)

(72) Inventors: Tatsuya Ohara, Hyogo (JP); Koutarou Muroyama, Hyogo (JP); Shinji Murosaki, Nara (JP); Yoshihiro Yamamoto, Hyogo (JP)

(73) Assignee: MORISHITA JINTAN CO., LTD., Osaka (JP)

( * ) Notice: Subject to any disclaimer, the term of this patent is extended or adjusted under 35 U.S.C. 154(b) by 0 days.

(21) Appl. No.: 14/378,895

(22) PCT Filed: Feb. 15, 2013

(86) PCT No.: PCT/JP2013/053768
§ 371 (c)(1),
(2) Date: Aug. 14, 2014

(87) PCT Pub. No.: WO2013/122235
PCT Pub. Date: Aug. 22, 2013

(65) Prior Publication Data
US 2015/0190448 A1    Jul. 9, 2015

(30) Foreign Application Priority Data

Feb. 15, 2012  (JP) ................. 2012-030291
Feb. 12, 2013  (JP) ................. 2013-024003
Feb. 15, 2013  (JP) ................. 2013-028446

(51) Int. Cl.
| | | |
|---|---|---|
| A61K 36/73 | (2006.01) |
| A61K 36/738 | (2006.01) |
| A23L 2/52 | (2006.01) |
| A61K 31/522 | (2006.01) |
| A61K 31/7048 | (2006.01) |
| A23K 10/30 | (2016.01) |
| A23K 20/111 | (2016.01) |
| A23K 20/10 | (2016.01) |
| A23L 33/10 | (2016.01) |
| A23L 33/105 | (2016.01) |

(52) U.S. Cl.
CPC ............ *A61K 36/738* (2013.01); *A23K 10/30* (2016.05); *A23K 20/10* (2016.05); *A23K 20/111* (2016.05); *A23L 2/52* (2013.01); *A23L 33/10* (2016.08); *A23L 33/105* (2016.08); *A61K 31/522* (2013.01); *A61K 31/7048* (2013.01); *A23V 2002/00* (2013.01)

(58) Field of Classification Search
CPC .................................................. A61K 36/738
See application file for complete search history.

(56) References Cited

U.S. PATENT DOCUMENTS

2008/0003312 A1    1/2008  Ninomiya et al.

FOREIGN PATENT DOCUMENTS

| CA | WO 2010054470 A1 * | 5/2010 | ........... A23L 1/3002 |
|---|---|---|---|
| DE | 32 34 366 | 3/1984 | |
| JP | 2006-016312 | 1/2006 | |
| JP | 3790767 | 1/2006 | |
| JP | 2007-176858 | 7/2007 | |
| JP | 4229942 | 7/2007 | |
| WO | 2010/054470 | 5/2010 | |

OTHER PUBLICATIONS

Andersson et al. (2011) Am. J. Physiol. Endocrinol. Metab. 300: E111-E121.*
Andersson et al. (2012) Eur. J. Clin. Nutr. 66: 585-590.*
Diepvens et al. (2007) Am. J. Physiol. Regul. Integr. Comp. Physiol. 292: R77-R85.*
Ford (2005) Diabetes Care 28: 1769-1778.*
Grundy et al. (2004) Circulation 109: 433-438.*
Nagatomo et al. (2015) Diabetes, Metabolic Syndrome and Obesity: Targets and Therapy, 8: 147-156.*
Ninomiya et al. (2007) Bioorganic and Medicinal Chemistry Letters 17: 3059-3064.*
Zheng et al. (2004) in vivo 18: 55-62.*
Chrubasik et al. (2008) Phytother. Res. 22, 725-733.*
Gao et al. (2000) J. Sci. Food Agric. 80: 2021-2027.*
Nagatomo et al. (2013) Prey. Nutr. Food Sci. 18(2): 85-91.*
Ninomiya et a. (2007) Bioorganic and Medicinal Chemistry Letters 17: 3059-3064.*
Wenzig et al. (2008) Phytomedicine 15: 826-835.*
Revilla et al. (1998) J. Agric. Food Chem. 46: 4592-4597.*
Inoue et al: "Regulation of the Body Fat Percentage in Developmental-Stage Rats by Methylxanthine Derivatives in a High-Fat Diet", Bioscience Biotechnology Biochemistry, Japan Society for Bioscience, Biotechnology, and Agrochemistry, Tokyo, Japan, vol. 70, No. 5, May 1, 2006, pp. 1134-1139, XP002468024, ISSN: 0916-8451, DOI: 10.1271/BBB.70.1134.
Goto et al: "Tiliroside, a glycosidic flavonoid, ameliorates obesity-induced metabolic disorders via activation of adiponectin signaling followed by enhancement of fatty acid oxidation in liver and skeletal muscle in obese-diabetic mice", The Journal of Nutritional Biochemistry, vol. 23, No. 7, Jul. 2012, pp. 768-776, XP002743777, ISSN: 1873-4847.
Extended European Search Report dated Sep. 11, 2015 in corresponding European Patent Application No. 13 74 9827.

(Continued)

*Primary Examiner* — Chris R Tate
*Assistant Examiner* — Russell Fiebig
(74) *Attorney, Agent, or Firm* — Wenderoth, Lind & Ponack, L.L.P.

(57) ABSTRACT

A primary object of the invention is to provide a composition for the prevention, amelioration, or treatment of metabolic syndrome and to provide a food or drink, a medicine, or a feed comprising the composition. A composition for the prevention, amelioration, or treatment of metabolic syndrome, the composition comprising the following (a) and (b):
(a) a rose hip extract, and
(b) at least a kind of xanthine derivatives.

7 Claims, No Drawings

(56) References Cited

OTHER PUBLICATIONS

International Preliminary Report on Patentability issued Aug. 19, 2014 in International (PCT) Application No. PCT/JP2013/053768.
Goto et al. "Tiliroside Improves Lipid Metabolism in Obesity Model Animals", Proceedings of the Annual Meeting of Japan Society for Bioscience, Biotechnology, and Agrochemistry, 2009, p. 222, with English translation.
Ninomiya et al., "Potent anti-obese principle from *Rosa canina*: Structural requirements and mode of action of *trans*-tiliroside", Bioorganic & Medicinal Chemistry Letters, vol. 17, Mar. 2007, pp. 3059-3064.
Dodd et al., "Caffeine and Exercise Performance", Sports Medicine, 1993, vol. 15, pp. 14-23.
Hollands et al., "A simple apparatus for comparative measurements of energy expenditure in human subjects: the thermic effect of caffeine", The American Journal of Clinical Nutrition, Oct. 1981, vol. 34, pp. 2291-2294.
International Search Report issued May 14, 2013 in International (PCT) Application No. PCT/JP2013/053768.

* cited by examiner

COMPOSITION FOR PREVENTION, AMELIORATION OR TREATMENT OF METABOLIC SYNDROME

TECHNICAL FIELD

The present invention relates to a composition for the prevention, amelioration, or treatment of metabolic syndrome. More specifically, the present invention relates to a composition comprising a rose hip extract and a xanthine derivative for the prevention, amelioration, or treatment of metabolic syndrome.

BACKGROUND ART

In recent years, with steadily increasing obesity, the World Health Organization (WHO) is warning countries around the world of an increased risk of lifestyle-related diseases, which are associated with obesity and include diabetes, hyperlipidemia, hypertension, arteriosclerosis, and fatty liver. Metabolic syndrome is a condition with, in addition to visceral fat accumulation, a combination of risk factors for arteriosclerosis, such as disorders of carbohydrate metabolism (abnormal glucose tolerance, diabetes), disorders of lipid metabolism (hypertriglyceridemia, hypercholesterolemia, and low levels of HDL cholesterol), and hypertension. Even if each of abnormalities (for example, in blood sugar or blood pressure) is mild and at the level of "Care Required" as a result of medical examination or the like, overlapping of such abnormalities tends to cause cardiovascular diseases. It is said that a human having 2 risk factors selected from obesity, hypertension, hyperglycemia, hypertriglyceridemia, and hypercholesterolemia is at the risk of cardiovascular diseases 10 times higher, and a human having 3 to 4 of such risk factors is at the risk 31 times higher as compared with a human not having any of such risk factors.

The co-occurrence of obesity, diabetes, hypertension, and hyperlipidemia increases the risk of developing myocardial infarction or cerebral infarction, and therefore is called "Deadly Quartet". Accumulation of visceral fat is considered to be the underlying cause eventually resulting in cardiovascular diseases, such as myocardial infarction and cerebral infarction. Therefore, for the prevention or amelioration of metabolic syndrome and also cardiovascular diseases, decreasing the accumulated visceral fat is important.

Since obesity is caused by an imbalance between energy intake and expenditure, it is important, for the purpose of inhibiting obesity, to not only decrease energy intake but also increase energy consumption in basal metabolism or activity metabolism. For decreasing energy intake, low-energy replacements for fat and sugar are provided, but the taste or processability thereof in terms of food is not necessarily satisfactory.

Various measures have been proposed for the prevention of obesity. In recent years, in different kinds of food we regularly take, components having an effect of improving lipid metabolism, or preventing or ameliorating obesity have been found, and are expected to be useful for the prevention of obesity.

The inventors focused attention on, among food components having such an effect, a rose hip extract and caffeine, which are known to have different working mechanisms with each other. It is reported that rose hip extracts have effects of reducing body weight, body fat percentage, and neutral fat in the liver (Patent Literature 1). It is also reported that the primary component providing the effects is tiliroside, which raises the expression level of the PPARα gene responsible for the reduction in the respiratory quotient and for fat combustion (Non Patent Literature 1 and 2). Meanwhile, caffeine is known to have an effect of reducing body fat and body weight by facilitating lipid metabolism (Non Patent Literature 3), by inhibiting hepatic lipogenesis, and by increasing resting metabolic rate and energy consumption (Non Patent Literature 4) via an effect of increasing circulating catecholamine level and an effect of inhibiting phosphodiesterase activity.

Thus, it is publicly known that each component by itself acts on lipid metabolism. However, there has been no report with regard to combining the components.

CITATION LIST

Patent Literature

Patent Literature 1: Japanese Patent No. 3790767

Non Patent Literature

Non Patent Literature 1:
Proceedings of the Annual Meeting of Japan Society for Bioscience, Biotechnology, and Agrochemistry 2009, p. 222
Non Patent Literature 2:
Ninomiya et al, Bioorganic & Medicinal Chemistry Letters, 2007, Vol. 17, 3059-3064
Non Patent Literature 3:
Dodd et al, Sports. Med., 1993, Vol. 15, 14-23
Non Patent Literature 4:
Hollands et al, Am. J. Clin. Nutr., 1981, Vol. 34, 2291-2294

SUMMARY OF INVENTION

Technical Problem

In order to prevent or decrease obesity, dietary therapy based on restricted calorie intake, exercise therapy, and medicinal therapy by use of an appetite suppressor, etc. are carried out. However, dietary therapy, which often involves excessively restricted diet, requires complicated calorie calculation and strong will, and therefore is difficult for an individual to manage for a long period of time. Also, exercise therapy, which is associated with mental and physical pain, is very difficult to continue for a long period of time in this busy modern society. It is effective to try to consume as much body fat as possible as energy source during exercise, but people with a tendency to become obese have slow fat metabolism, and it is difficult for them to decrease body fat by exercise. Accordingly, development of a composition that can contribute to the prevention or amelioration of obesity by inhibiting hepatic lipogenesis, facilitating resolution of fat accumulated in fat cells, and effectively burning fat, and a food or drink or a medicine comprising the composition has been desired.

The present invention was made in light of the above-mentioned problems, and the objective of the invention includes providing a composition for the prevention, amelioration, or treatment of metabolic syndrome and providing a food or drink, a medicine, or a feed comprising the composition.

Solution to Problem

After intensive investigations into compositions which effectively decrease body fat, the present inventors found that a composition comprising a rose hip extract and caffeine has a fat-reducing effect which is surprisingly stronger than the effect exhibited when each of the components is used alone. The inventors have carried out further investigations and completed the present invention.

That is, the present invention relates to the following.

[1] A composition for the prevention, amelioration, or treatment of metabolic syndrome, the composition comprising the following (a) and (b):
(a) a rose hip extract, and
(b) at least a kind of xanthine derivatives.
[2] The composition according to the above [1], wherein the rose hip extract contains, as an active ingredient, a polar solvent extract of a rose hip fruit containing seeds.
[3] The composition according to the above [1] or [2], wherein the xanthine derivative is caffeine, theophylline, or theobromine.
[4] The composition according to any one of the above [1] to [3], wherein the rose hip extract contains, as an active ingredient, tiliroside having the structure of the following Formula (1):

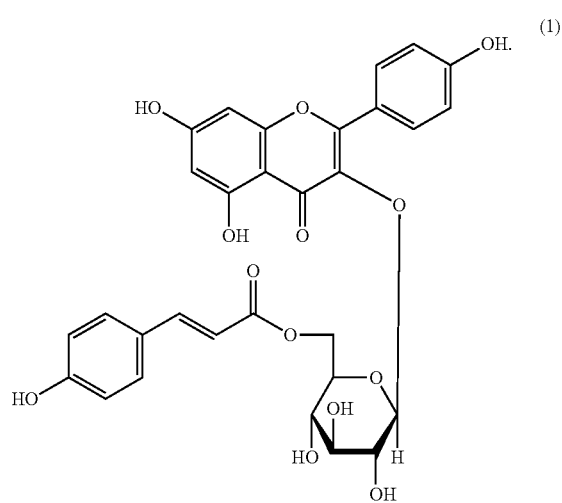

[5] The composition according to any one of the above [1] to [4], wherein the mass ratio between (a) and (b) is 1000:1 to 0.1:1.
[6] The composition according to any one of the above [1] to [5], wherein the mass ratio between (a) and (b) is 100:1 to 1:1.
[7] A medicine, a food or drink, or a feed comprising the composition according to any one of the above [1] to [6].
[8] A method for the prevention, amelioration, or treatment of metabolic syndrome, the method comprising the step of administering, to an animal or a human, a composition comprising (a) and (b):
(a) a rose hip extract, and
(b) at least a kind of xanthine derivatives.
[9] The method according to the above [8], wherein the rose hip extract contains, as an active ingredient, a polar solvent extract of a rose hip fruit containing seeds.
[10] The method according to the above [8] or [9], wherein the xanthine derivative is caffeine, theophylline, or theobromine.
[11] The method according to any one of the above [8] to [10], wherein the rose hip extract contains, as an active ingredient, tiliroside having the structure of the following Formula (1):

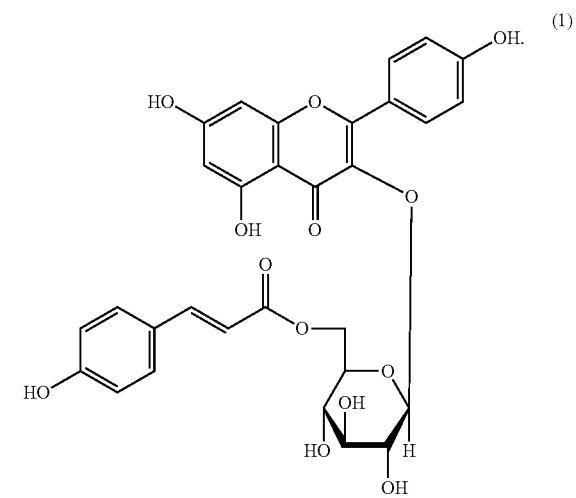

[12] The method according to any one of the above [8] to [11], wherein the mass ratio between (a) and (b) is 1000:1 to 0.1:1.
[13] The method according to any one of the above [8] to [12], wherein the mass ratio between (a) and (b) is 100:1 to 1:1.
[14] The method according to any one of the above [8] to [13], wherein the composition is a medicine, a food or drink, or a feed.
[15] Use of a composition comprising (a) and (b):
(a) a rose hip extract, and
(b) at least a kind of xanthine derivatives
for the prevention, amelioration, or treatment of metabolic syndrome.
[16] The use according to the above [15], wherein the rose hip extract contains, as an active ingredient, a polar solvent extract of a rose hip fruit containing seeds.
[17] The use according to the above [15] or [16], wherein the xanthine derivative is caffeine, theophylline, or theobromine.
[18] The use according to any one of the above [15] to [17], wherein the rose hip extract contains, as an active ingredient, tiliroside having the structure of the following Formula (1):

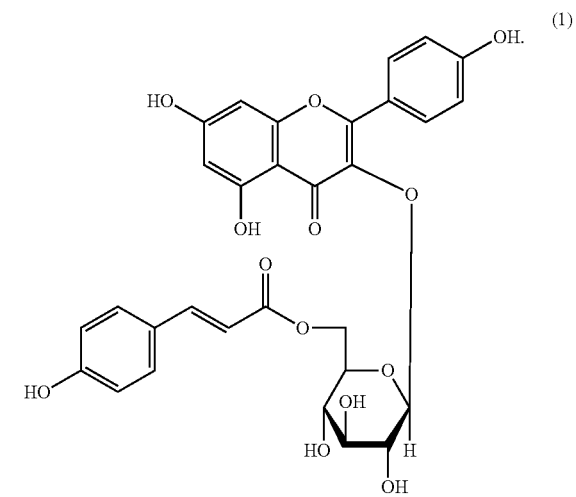

[19] The use according to any one of the above [15] to [18], wherein the mass ratio between (a) and (b) is 1000:1 to 0.1:1.
[20] The use according to any one of the above [15] to [19], wherein the mass ratio between (a) and (b) is 100:1 to 1:1.
[21] The use according to the above [15] to [20], wherein the composition is a medicine, a food or drink, or a feed.
[22] Use of a composition comprising (a) and (b):
(a) a rose hip extract, and
(b) at least a kind of xanthine derivatives
for producing a medicine for the prevention, amelioration, or treatment of metabolic syndrome.
[23] The use of the composition according to the above [22], wherein the rose hip extract contains, as an active ingredient, a polar solvent extract of a rose hip fruit containing seeds.
[24] The use according to the above [22] or [23], wherein the xanthine derivative is caffeine, theophylline, or theobromine.
[25] The use according to any one of the above [22] to [24], wherein the rose hip extract contains, as an active ingredient, tiliroside having the structure of the following Formula (1):

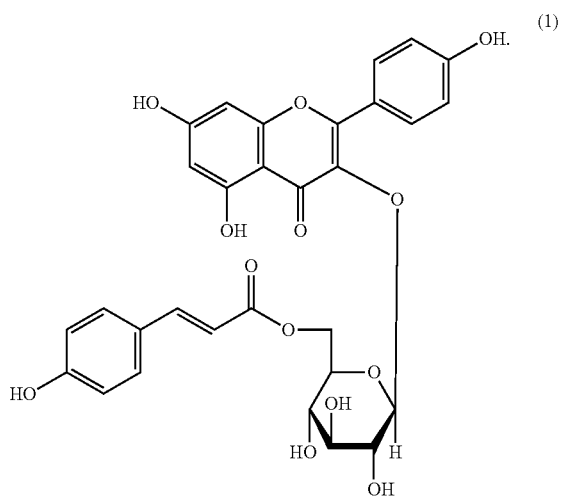

[26] The use according to any one of the above [22] to [25], wherein the mass ratio between (a) and (b) is 1000:1 to 0.1:1.
[27] The use according to any one of the above [22] to [26], wherein the mass ratio between (a) and (b) is 100:1 to 1:1.
[28] The use according to any one of the above [22] to [27], wherein the composition is a medicine, a food or drink, or a feed.

Advantageous Effects of Invention

The use of the composition of the present invention enables the prevention, amelioration, or treatment of metabolic syndrome. More specifically, the use enables, in addition to fat reduction, body weight reduction, and the prevention, amelioration, or treatment of obesity, also the prevention, amelioration, or treatment of diabetes, hypertriglyceridemia, hypercholesterolemia, and arteriosclerosis, which are considered to result from visceral fat accumulation.

DESCRIPTION OF EMBODIMENTS

The present invention provides a composition for the prevention, amelioration, or treatment of metabolic syndrome, the composition comprising (a) and (b):

(a) a rose hip extract, and
(b) at least a kind of xanthine derivatives,
the mass ratio between (a) and (b) being preferably 1000:1 to 1:0.1.

Rose Hip Extract

Arose hip extract means an extract obtained by extraction of rose hip with use of a solvent, a diluted or concentrated liquid thereof, or a dried matter thereof. Various forms of the dried matter will be described later.

The rose hip means the flowers, stems, bulbs, roots, seeds (pseudocarps), episperms, pericarps, flesh, etc. of *Rosa canina, Rosa centifolia, Rosa rugosa*, etc., which belong to the genus *Rosa*, in the form of a dried, broken, crushed, or pulverized material, a dried powder thereof, a shaped product of the dried powder, or the like. In particular, use of the rose hip fruit containing the seeds (pseudocarps) is preferable and use of the seeds (pseudocarps) of rose hip is still more preferable.

The solvent used for the extraction may be a polar solvent or a nonpolar solvent. Examples of the solvent to be used for the extraction include water; alcohols, such as methanol, ethanol, 1-propanol, 2-propanol, 1-butanol, and 2-butanol; ethers, such as dimethylether, diethylether, diglyme, and tetrahydrofuran; esters, such as methyl acetate and ethyl acetate; ketones, such as acetone and methylethyl ketone; nitriles, such as acetonitrile and propionitrile; hydrocarbons, such as heptane, hexane, and cyclohexane; aromatic hydrocarbons, such as benzene and toluene; and halogenated aliphatic hydrocarbons, such as methylene chloride and chloroform. The solvents may be used alone or in combination of two or more kinds thereof.

The solvent to be used for the extraction is preferably a polar solvent. More preferred is an alcohol, an ester, or water used alone or as a mixture of two or more kinds thereof; still more preferred is a lower alcohol having 1 to 6 carbon atoms, such as ethanol, 1-propanol, 2-propanol, 1-butanol, and 2-butanol, ethyl acetate, or water used alone or as a mixture of two or more kinds thereof; and particularly preferred is a mixed solution of ethanol and water.

In cases where a mixed solution of a lower alcohol having 1 to 6 carbon atoms and water is used as a solvent for the extraction, the mixing ratio is not particularly limited. For example, the ratio is 99.9:0.1 to 0.1:99.9, preferably 95:5 to 5:95, more preferably 80:20 to 20:80, and particularly preferably 80:20 to 51:49 by volume.

The method for the extraction of the rose hip is not particularly limited, but the extraction is preferably performed under mild conditions for ensuring the safety of the extract and for reducing the production cost and the loss of nutritional components. The extraction of the rose hip can be performed, for example, as follows: a rose hip fruit containing seeds is pulverized, crushed or cut; a solvent in an amount of 5 to 20 times the volume of the rose hip is added thereto; and the extraction is performed at 0° C. to the reflux temperature of the solvent for 30 minutes to 48 hours under the condition of shaking, stirring, or reflux. After the extraction, separation operation, such as filtration and centrifugal separation may be performed to remove insoluble matters and give an extract. Extraction may be repeated with use of the removed insoluble matters, and the obtained extracts may be combined.

The rose hip extract may be used as it is or used after dilution or concentration as needed. The extract may be any form of a liquid, a concentrate, and a paste, and also may be in the dried form thereof.

In the drying of the rose hip extract, the above-mentioned liquid, concentrate, or paste as it is may be subjected to drying process to give a powder or a solid matter. The drying can be performed by an ordinary method usually employed by a person skilled in the art, such as spray drying, freeze-drying, reduced-pressure drying, or fluidized drying.

Tiliroside

The rose hip extract preferably contains, as an active ingredient, tiliroside represented by the following Formula (1):

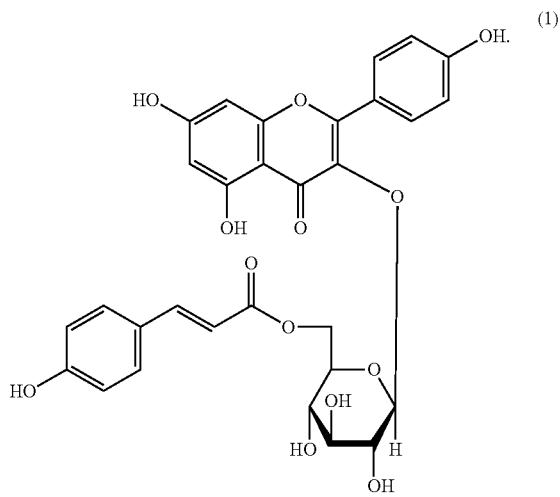

Tiliroside is a kind of polyphenols. Tiliroside has an effect of activating an enzyme responsible for enhancing β oxidation in the body, and as a result enhances the metabolism of body fat (in particular, fat accumulated in the viscera). In addition, tiliroside raises the expression level of the PPARα gene responsible for the reduction in the respiratory quotient and for fat combustion, and therefore increases the metabolism of body fat. Further, tiliroside also exhibits an excellent effect of improving glucose tolerance. Accordingly, tiliroside exhibits an excellent effect on the prevention, amelioration, and treatment of various kinds of diseases resulting from obesity etc., metabolic syndrome, and the like.

The tiliroside content is not particularly limited, but is preferably 0.01 mass % or more, more preferably 0.02% or more, and still more preferably 0.04% or more on dry basis.

In the present invention "visceral fat" means the fat accumulated on the organs inside the abdominal cavity, such as the liver, the kidney, the pancreas, and the intestines, and the areas therearound (for example, areas around the liver, the mesentery, etc.) including epididymal fat.

Xanthine Derivative

The xanthine derivative to be used for the present invention is not particularly limited, and examples thereof include a compound represented by the following Formula (2):

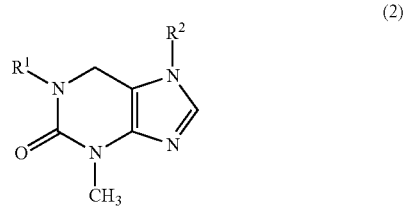

(wherein $R^1$ represents a methyl group or a hydrogen atom, and $R^2$ represents a hydrogen atom or an alkyl group having 1 to 12 carbon atoms optionally substituted by 1 or 2 hydroxy groups or an alkanoyl group having 2 to 10 carbon atoms) or a salt thereof.

Examples of the xanthine derivatives include xanthin, aminophylline, theophylline, choline theophylline, caffeine, theobromine, 1,7-dimethylxanthin, oxtriphylline, diprophylline, and proxyphylline. Inter alia, caffeine, theophylline, and theobromine are preferred, and caffeine is more preferred.

The component (b) may be any one kind or a combination of two or more kinds of the xanthine derivatives exemplified above. These xanthine derivatives may be synthesized by a publicly known method or extracted from tea leaves, coffee beans, etc.

Other Components

The composition of the present invention may contain, as optional components, a substance which inhibits the synthesis of neutral fat (for example, Salacia and green tea, which have an activity of inhibiting fat synthesis enzymes), a substance which has an effect of inhibiting fat absorption (for example, rosemary, sage, ginger, mango ginger, and cucumber, which inhibit the activity of digestive tract lipase), a substance which enhances the release of fat from fat cells into the blood (for example, citrus, hibiscus, bitter melon, conjugated linoleic acid, etc.), and a substance which has an effect of inhibiting alcohol absorption (for example, laurel, horse-chestnut conkers, and the shoots of Aralia elata). These substances may be used as they are or used after concentration, extraction, drying, etc.

The composition of the present invention may further contain carnitine.

When containing the above components, the composition of the present invention can exhibit a further increased fat-reducing effect and a slimming effect.

The composition of the present invention can be used as a medicine, a food or drink, a feed, a food additive, a feed additive, or the like. The composition is particularly preferable for use in a medicine, a food or drink, or a feed.

A medicine comprising the composition of the present invention may be orally or parenterally administered to a mammal. Examples of oral preparations include a granule, a powder, a tablet (including a sugar-coated tablet), a pill, a capsule, a syrup, an emulsion, and a suspension. Examples of parenteral preparations include injections (for example, a subcutaneous injection, an intravenous injection, an intramuscular injection, and an intraperitoneal injection), an intravenous fluid, external preparations (for example, an intranasal preparation, a transdermal preparation, and an ointment), and suppositories (for example, an intrarectal suppository and an intravaginal suppository). These preparations can be formulated with use of a pharmaceutically acceptable carrier by a method conventionally used in the art. Examples of the pharmaceutically acceptable carrier include an excipient, a binder, a diluent, an additive, a flavor, a buffer, a thickener, a colorant, a stabilizer, an emulsifier, a dispersant, a suspending agent, a preservative, and the like. In particular, magnesium carbonate, magnesium stearate, talc, sugar, lactose, pectin, dextrin, starch, gelatin, tragacanth, methylcellulose, sodium carboxymethylcellulose, low-melting-point wax, cacao butter, or the like can be used.

Oral solid preparations (for example, a tablet, a pill, a capsule, a powder, a granule, or the like) can be formulated by a conventional means including mixing the active ingredient with an excipient (for example, lactose, mannitol, glucose, microcrystalline cellulose, starch, or the like), a binder (for example, hydroxypropylcellulose, polyvinyl pyrrolidone, magnesium aluminometasilicate, or the like), a disintegrant (for example, calcium cellulose glycolate, or the like), a lubricant (for example, magnesium stearate, or the like), a stabilizer, a solubilizer (for example, glutamic acid, aspartic acid, or the like), or the like. As needed, such preparations may be coated with a coating agent (for example, saccharose, gelatin, hydroxypropylcellulose, hydroxypropyl methylcellulose phthalate, or the like), and the coating may consist of 2 or more layers.

Oral liquid preparations (for example, a solution, a suspension, an emulsion, a syrup, an elixir, or the like) are formulated by dissolving, suspending, or emulsifying the active ingredient in a generally used diluent (for example, purified water, ethanol, or a mixture thereof, or the like). The liquid preparation may further comprise a wetting agent, a suspending agent, an emulsifier, a sweetener, a flavor, a fragrance, a preservative, a buffer, or the like.

Injections include a solution, a suspension, an emulsion, and a solid injection to be dissolved or suspended in a solvent before use. Injections are formulated by dissolving, suspending, or emulsifying the active ingredient in a solvent. As the solvent, for example, distilled water for injection; physiological saline; a vegetable oil; alcohols, such as propylene glycol, polyethylene glycol, and ethanol; and a combination thereof may be used. The injection may further comprise a stabilizer, a solubilizer (for example, glutamic acid, aspartic acid, Polysorbate 80 (registered trademark), or the like), a suspending agent, an emulsifier, a soothing agent, a buffer, a preservative, or the like. These injections are sterilized in the final step or produced by aseptic manipulation. The injection may be produced in a form of a sterile solid preparation, for example a lyophilized product, which can be dissolved in sterilized or sterile distilled water for injection or in another sterilized or sterile solvent just before use.

To a food or drink comprising the composition of the present invention, food additives generally used in a food or drink may be added, and examples thereof include a sweetener, a colorant, a preservative, a thickener, an antioxidant, a color improver, a decolorant, an antifungal agent, a gum base, a bittering agent, an enzyme, a brightener, an acidulant, a seasoning, an emulsifier, a fortifier, a processing aid, a flavor, a spice extract, etc. The food or drink includes a health food, a functional food, a food for specified health use, and a food for babies, toddlers, pregnant or nursing mothers, or the sick.

The food or drink suitable for the present invention is not particularly limited. Specific examples thereof include so-called dietary supplements in the form of a tablet, a granule, a powder, or a health drink. Other examples include drinks, such as tea drink, refreshing drink, carbonated drink, nutritional drink, fruit juice, and lactic drink; noodles, such as buckwheat noodle, wheat noodle, Chinese noodle, and instant noodle; sweets and bakery products, such as drop, candy, gum, chocolate, snack, biscuit, jelly, jam, cream, pastry, and bread; fishery or livestock products, such as fish sausage, ham, and sausage; dairy products, such as processed milk and fermented milk; fats, oils, and processed foods thereof, such as vegetable oil, oil for deep frying, margarine, mayonnaise, shortening, whipped cream, and dressing; seasonings, such as sauce and dipping sauce; retort pouch foods, such as curry, stew, rice-bowl cuisine, porridge, and rice soup; and frozen desserts, such as ice cream, sherbet, and shaved ice.

In light of the effects of the composition of the present invention, a food or drink prepared with use of the composition may be labeled as improving lipid metabolism; promoting basal metabolism; reducing body weight; reducing visceral fat or subcutaneous fat; having a slimming effect; preventing or treating obesity, or ameliorating a symptom thereof; and/or preventing or treating metabolic syndrome, or ameliorating a symptom thereof.

Examples of the feed comprising the composition of the present invention include a feed for livestock such as a cow, a horse, a pig, a sheep, a rabbit, and a goat; a feed for poultry such as a chicken, a duck, a goose, a turkey, a quail, an ostrich, and a pheasant; and a feed for pet animals, such as a dog, a cat, a rat, and a mouse. The feed comprising the composition of the present invention can be prepared by adding the composition to a feed, or processed and produced with use of an ordinary production method.

The amount of administration or intake of the medicine or the food or drink of the present invention may be determined depending on the age and body weight of the patient or ingester, symptoms, the administration time, the dosage form, the administration method, the combination of medicines, or the like. For example, preferred is that administration or intake is performed so that 0.2 to 100 g, preferably 0.2 to 20 g of the component (a) in terms of dry mass and 0.01 to 0.5 g, preferably 0.05 to 0.3 g of the component (b) are daily given to an adult human. Such a daily amount may be given in a single dose or in several divided doses.

The mass ratio between the component (a) and the component (b) is 1000:1 to 0.1:1, preferably 500:1 to 0.2:1, more preferably 250:1 to 0.5:1, and particularly preferably 100:1 to 1:1. This range may be 1000:1 to 1:0.1, 500:1 to 1:0.5, or 250:1 to 1:1. The mass ranges of 1000:1 to 1:1 and 250:1 to 1:0.1 are also of importance.

When the mass ratio between the component (a) and the component (b) is in the above range, the composition of the present invention can exhibit an excellent effect of preventing, ameliorating, or treating metabolic syndrome.

EXAMPLES

Hereinafter, the present invention will be illustrated in more detail by Examples and Test Examples, but the present invention is not limited thereto. The "part" in the Examples is on weight basis.

Example 1.1

Production of Seamless Capsules

RHP (10 parts) and caffeine (0.5 part) were suspended in a soybean oil (400 parts) to give the liquid content of seamless capsules. To obtain a shell material suspension to be used for the preparation of the outer layer of the seamless capsules, gelatin (35 parts) and D-sorbitol (10 parts) were added to distilled water (200 parts) and stirred at 60° C. to be suspended therein. The content liquid and the shell material suspension heated to 60° C. were simultaneously extruded from the inner nozzle and the outer nozzle of a double tube nozzle, respectively, and thus formed double-layer droplets were dropped into a solidifying oil at 12° C. for cooling to give wet capsules. After removing the solidification oil from the obtained wet capsules, drying in a drum drier was performed. Thus, the seamless capsules with a particle diameter of 2 mm were obtained.

Example 1.2

Production of Soft Capsules

RHP (10 parts) and caffeine (1 part) were suspended in a rapeseed oil (400 parts) to give the content liquid of soft capsules. To obtain gelatin films to be used for the shell of the soft capsules, gelatin (4 parts) and glycerin (1 part) were added to distilled water (2 parts), stirred at 60° C. to be suspended therein, and formed into sheets. The gelatin films were supplied between a pair of rotary die cylinders and the content liquid was extruded between the gelatin films with use of a pump synchronized with the dies to prepare the capsules.

Example 1.3

Production of Hard Capsules

RHP (10 parts) and caffeine (2 parts) were dispersed in corn starch (300 parts) to give the content of hard capsules. As the hard capsule shells, commercially available capsules in size 5 as specified in the Japanese Pharmacopoeia were used. The capsule shells were filled with the content in a usual manner to give hard capsules.

Example 1.4

Production of Tablets

RHP (10 parts), caffeine (5 parts), cornstarch (45 parts), and carboxymethylcellulose calcium (20 parts) were fed into a tumbling granulator and then mixed with preheating. After a solution (34 parts) containing hydroxypropylcellulose (1.7 parts) was sprayed thereonto, a granulated powder was obtained. Carboxymethylcellulose calcium (100 parts) and talc (40 parts) were added to and mixed with the obtained granulated powder, and the mixed powder was tableted with a tableting machine to give tablets.

Example 1.5

Production of Granules

In the same manner as in Example 1.4, a granulated powder containing lactose, corn starch, and carboxymethylcellulose calcium and being coated with hydroxypropylcellulose was obtained. The granulated powder was processed in an extruder to give granules.

Example 1.6

Production of Drink

RHP (10 parts), hydrolyzed starch (1 part), caffeine (0.1 part), and a flavor (appropriate amount) were dissolved in purified water (100 parts) to give a drink.

<Test Method>

Mice were fed with a high-calorie feed for the preparation of diet-induced obese mice. The calorie intake of the diet-induced obese mice was restricted so as to induce a state of facilitated resolution and utilization of body fat, and then the composition of the present invention containing a rose hip extract and caffeine was given to the mice. In this way, examination was conducted to determine whether the composition could facilitate the resolution and utilization of body fat and thereby ameliorate obesity.

The rose hip extract used was "Rose hip polyphenol EX (trade name)" (tiliroside content: 0.1% by mass or higher, made by Morishita Jintan Co., Ltd., hereinafter abbreviated to RHP).

The caffeine used was "*Chanomoto* (trade name)" (purity of caffeine: 98.5%, made by Shiratori Pharmaceutical Co., Ltd.). The powder feed for breeding used was "CE-2" (trade name, made by CLEA Japan, Inc.).

The high-calorie feed (4.73 kcal/g) and the low-calorie feed (3.16 kcal/g) used had the compositions as shown in Table 1 below.

Other compositions, reagents, and instruments used in Test Examples below were commercial products unless otherwise stated.

TABLE 1

Compositions of high-calorie feed and low-calorie feed (Unit: mass %)

| Composition | High-calorie feed | Low-calorie feed |
|---|---|---|
| Corn starch | 53.25 | 53.25 |
| Casein | 18.00 | 18.00 |
| Corn oil | 20.00 | 2.50 |
| Cellulose | 2.50 | 20.00 |
| AIN93G Mineral Mix[1] | 5.00 | 5.00 |
| AIN93 Vitamin Mix[1] | 1.00 | 1.00 |
| Choline bitartrate | 0.25 | 0.25 |
| Calorie (kcal/g) | 4.73 | 3.16 |

[1] Made by Oriental Yeast Co., Ltd.

Test Example 1

Five-week-old male KK mice were fed with water and the powder feed for breeding for three days, and then fed with the high-calorie feed for 3 weeks for the preparation of diet-induced obese mice. The diet-induced obese mice were divided into three groups (six mice per group) and fed with the feed (1) to (3) shown below for 2 weeks. The feeds given to the test groups are as follows.

(1) Control group; low-calorie feed
(2) 0.25% RHP administration group; low-calorie feed+0.25 mass % of RHP
(3) 0.50% RHP administration group; low-calorie feed+0.50 mass % of RHP During the test period (2 weeks from the start of low-calorie feeding), the body weight and feed intake of the mice were periodically measured. After the end of the test, the mice were euthanized, and epididymal fat tissue was harvested and weighed.

The body weight of the mice on the last day of the test (g), the average calorie intake per day (kcal/day) in the test period (12 days), and the weight of epididymal (visceral) fat per 100 g of body weight (g/100 g body weight) are shown in Table 2. The results are shown as the mean±SD of each group.

TABLE 2

| | | Results | | |
|---|---|---|---|---|
| | Composition RHP (mass %) | Calorie intake (kcal/day) | Body weight (g) | Epididymal fat weight (g/100 g body weight) |
| (1) Control group | 0 | 14.8 ± 0.9 | 37.9 ± 0.5 | 1.71 ± 0.18 |
| (2) 0.25% RHP group | 0.25 | 14.7 ± 0.7 | 38.2 ± 0.7 | 1.79 ± 0.11 |
| (3) 0.50% RHP group | 0.50 | 14.6 ± 0.8 | 38.0 ± 0.9 | 1.70 ± 0.04 |

As shown in Table 2, regarding the weight of epididymal fat, the 0.25% RHP administration group (2) did not show any fat-reducing effect as compared with the control group (1). Also, the 0.50% RHP administration group (3) did not show any statistically significant fat-reducing effect.

Test Example 2

Diet-induced obese mice were divided into four groups (six mice per group) and fed with the feed (4) to (7) shown below. Other test conditions were the same as in Test Example 1.
(4) Control group; low-calorie feed
(5) 2.5% RHP administration group; low-calorie feed+2.5 mass % of RHP
(6) 0.025% caffeine administration group; low-calorie feed+ 0.025 mass % of caffeine
(7) Present invention product (mixture of RHP and caffeine (20:1)) administration group; low-calorie feed+0.50 mass % of RHP+0.025 mass % of caffeine)
The above mixing ratio of each mixture is a ratio by weight.

The results are shown in Table 3. The results in Table 3 were statistically analyzed by Dunnett's multiple comparison test. The symbol ** indicates a significant difference with a risk less than 1% from the control group.

TABLE 3

| | Composition | | Results | | |
|---|---|---|---|---|---|
| | RHP (mass %) | Caffeine (mass %) | Calorie intake (kcal/day) | Body weight (g) | Epididymal fat weight (g/100 g body weight) |
| (4) Control group | 0 | 0 | 13.7 ± 0.6 | 36.6 ± 1.1 | 1.76 ± 0.19 |
| (5) 2.5% RHP group | 2.5 | 0 | 13.9 ± 1.0 | 36.7 ± 1.9 | 1.58 ± 0.19 |
| (6) 0.025% caffeine group | 0 | 0.025 | 13.5 ± 1.3 | 35.2 ± 1.8 | 1.60 ± 0.19 |
| (7) Present invention product group | 0.5 | 0.025 | 14.5 ± 1.2 | 35.9 ± 1.5 | 1.37 ± 0.16** |

As shown in Table 3, regarding the weight of epididymal fat tissue, the 2.5% RHP administration group (5) showed 10.2% reduction as compared with the control group (4). Similarly, the 0.025% caffeine administration group (6) showed 9.2% reduction as compared with the control group (4). However, none of them showed any statistically significant fat-reducing effect.

Meanwhile, the present invention product administration group (7), to which 0.025% caffeine and 0.50% RHP in combination were administered, showed 21.9% reduction in the weight of epididymal fat tissue, which indicated a statistically significant fat-reducing effect.

The results revealed that the present invention product administration group (7) showed an excellent fat-reducing effect unpredictable from the cases where 0.025% caffeine or 0.50% RHP was administered alone.

All the above results revealed that the composition of the present invention comprising both a rose, hip extract and caffeine exhibited a clear synergistic effect and reduced the amount of visceral fat. The results also showed that, since the composition of the present invention has a visceral-fat-reducing effect, a medicine, a food or drink, or a feed which comprises the composition of the present invention is useful for the prevention, amelioration, or treatment of metabolic syndrome.

INDUSTRIAL APPLICABILITY

The composition of the present invention has an effect of preventing, ameliorating, or treating metabolic syndrome, and therefore is useful in industrial applications.

The invention claimed is:
1. A method for the amelioration or treatment of metabolic syndrome, the method comprising the step of administering, to an animal or a human in need thereof, an effective amount of a composition consisting essentially of (a) and (b):
    (a) a rose hip extract, and
    (b) caffeine,
        wherein the mass ratio between (a) and (b) is 20:1, and
        wherein the rose hip extract comprises, as an active ingredient, 0.01 mass % or more on a dry basis of tiliroside having the structure of the following Formula (1):

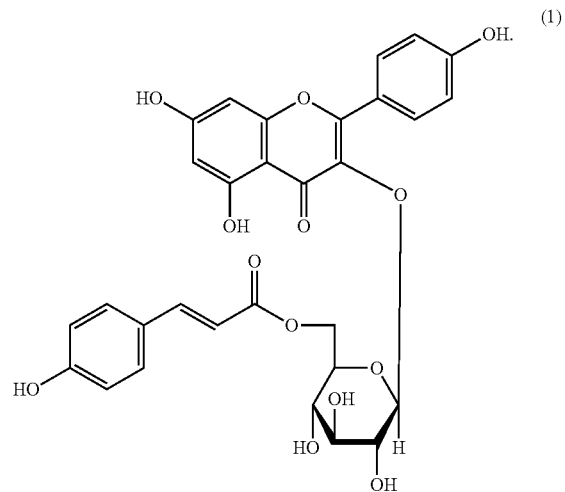

2. The method according to claim 1, wherein the rose hip extract is obtained by extraction of a seed-containing rose hip fruit with a polar solvent, and wherein the polar solvent is a mixture of water and a lower alcohol having 1 to 6 carbon atoms.
3. The method according to claim 2, wherein the extraction is performed at a temperature of 50° C. to the reflux temperature of the solvent for 30 minutes to 6 hours under reflux, wherein the polar solvent is used in an amount of 5 to 20 times the volume of the rose hip fruit, and wherein the mixing ratio of the lower alcohol having 1 to 6 carbon atoms and water is 30:70 to 70:30.
4. The method according to claim 2, wherein the polar solvent is ethanol, 1-propanol, 2-propanol, 1-butanol or 2-butanol.
5. The method according to claim 1, wherein the rose hip extract comprises, as an active ingredient, 0.1 mass % or more on a dry basis of tiliroside having the structure of Formula (1).
6. The method according to claim 1, wherein the rose hip extract comprises, as an active ingredient, said tiliroside in an amount of 0.1153 mass % on a dry basis.
7. The method according to claim 1, wherein the composition is a medicine, a food or drink, or a feed.

* * * * *